(12) United States Patent
Cotticelli et al.

(10) Patent No.: US 7,482,477 B2
(45) Date of Patent: Jan. 27, 2009

(54) PROCESS FOR THE PREPARATION OF CITALOPRAM AND ESCITALOPRAM

(75) Inventors: Giovanni Cotticelli, Cernusco sul Naviglio (IT); Raul Salvetti, Malonno (IT)

(73) Assignee: Adorkem Technology SPA, Costa Volpino (IT)

( * ) Notice: Subject to any disclaimer, the term of this patent is extended or adjusted under 35 U.S.C. 154(b) by 0 days.

(21) Appl. No.: 11/664,317

(22) PCT Filed: Sep. 14, 2005

(86) PCT No.: PCT/EP2005/054566

§ 371 (c)(1),
(2), (4) Date: Jul. 19, 2007

(87) PCT Pub. No.: WO2006/037714

PCT Pub. Date: Apr. 13, 2006

(65) Prior Publication Data

US 2007/0270599 A1     Nov. 22, 2007

(30) Foreign Application Priority Data

Oct. 1, 2004    (IT)  ................ MI2004A1872

(51) Int. Cl.
    *C07D 307/87*    (2006.01)
(52) U.S. Cl. ...................... 549/467; 435/126

(58) Field of Classification Search ............ 549/467
See application file for complete search history.

(56) References Cited

U.S. PATENT DOCUMENTS 4,650,884 A     3/1987   Bogeso et al.

FOREIGN PATENT DOCUMENTS

| EP | 0 347 066 A | 12/1989 |
|---|---|---|
| WO | WO 03/006449 A | 1/2003 |
| WO | WO 2004/014821 A | 2/2004 |
| WO | WO 2004/056754 A | 7/2004 |
| WO | WO 2005/098018 A | 4/2005 |

OTHER PUBLICATIONS

Carlock et al., Tetrahedron Letters, 19(52): 5153-5156 (1978).
Mitsunobu, O., Georg Thieme Verlag, Stuttgart, Germany, 1-28 (1981).
Solares, L.F., et al, Tetrahedron: Asymmetry, Elsevier Science Publishers, Amsterdam, NL, 341-345 (2004).

*Primary Examiner*—Bernard Dentz
(74) *Attorney, Agent, or Firm*—Perkins Coie LLP

(57) ABSTRACT

A process is described for the preparation of citalopram (I) and of the active enantiomer thereof, escitalopram (II), which process comprises the cyclisation reaction of the corresponding precursor diol of the formula III or, respectively, IV in the presence of an azodicarboxylate, a phosphine and a strong base.

21 Claims, No Drawings

PROCESS FOR THE PREPARATION OF CITALOPRAM AND ESCITALOPRAM

CROSS-REFERENCE TO RELATED APPLICATIONS

This application is a 35 U.S.C. §371 application of International Application No. PCT/EP2005/054566 filed Sep. 14, 2005, designating the U.S., which claims the benefit of priority of Italian Application No. MI2004A001872, filed Oct. 1, 2004.

The present invention relates to a process for the preparation of 1-(3-dimethylaminopropyl)-1-(4'-fluorophenyl)-1,3-dihydro-5-isobenzofurancarbonitrile, better known under the name citalopram, of the formula

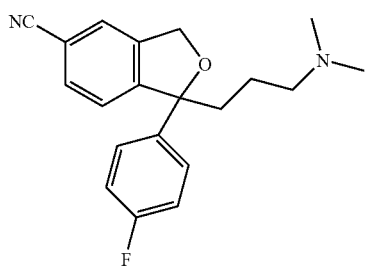
(I)

and, in particular, of the enantiomer thereof S(+)-1-(3-dimethylaminopropyl)-1-(4'-fluorophenyl)-1,3-dihydro-5-isobenzofurancarbonitrile, known under the name escitalopram, of the formula

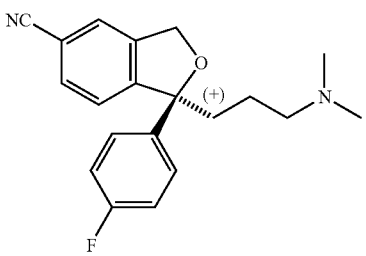
(II)

These compounds are known active ingredients (Merck Index 1996, no. 2379), commonly used for the treatment of depression. In this connection, it has been known for some time that virtually the entirety of the pharmacological activity of citalopram (I) resides in the S(+) enantiomer, namely escitalopram (II).

PRIOR ART

The literature reports numerous processes for the preparation of these compounds and, among these, those which are particularly relevant in the present context are those which provide the cyclisation reaction by means of dehydration of the compound of the formula

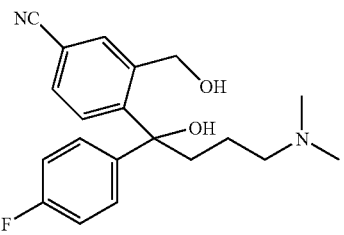
(III)

to yield citalopram (I), and of the compound of the formula

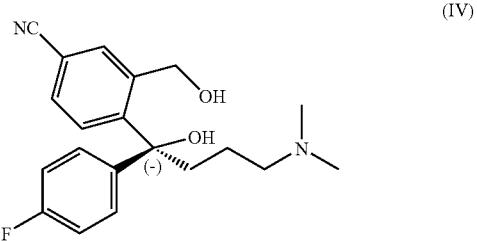
(IV)

to yield escitalopram (II).

The synthesis of citalopram from compound (III) is described, for example, in U.S. Pat. No. 4,650,884, in which the above-mentioned cyclisation is performed under somewhat severe conditions, namely with 70% strength sulfuric acid and heating to 80° C. for 3 hours. The use of hot sulfuric acid, a reactant which is not easily handled industrially, results in degradation of the substrate and reduced reaction yields. Less severe, non-racemising conditions have been developed for the preparation of escitalopram (II) involving closure of the optically active diol (IV), for example by treatment with mesyl chloride and triethylamine, as described in EP347066. This method, which can obviously also be applied to the preparation of citalopram (I), does, however, exhibit the non-negligible disadvantage of using an acid chloride, namely a type of reactant which is well known to be difficult to handle and to be unstable in air. Indeed, due to the sensitivity to atmospheric conditions and thus the possible partial decomposition of said reactant, the reaction may prove to be non-reproducible on an industrial scale.

We have now found a process for the preparation of citalopram (I) and, preferably, of escitalopram (II) by cyclisation of the precursor diols (III) and, respectively, (IV), which makes it possible to obtain said products at high yields, under conditions which are mild and reproducible and, in the case of escitalopram, non-racemising.

SUMMARY OF THE INVENTION

The present invention accordingly provides a process for the preparation of citalopram of the formula

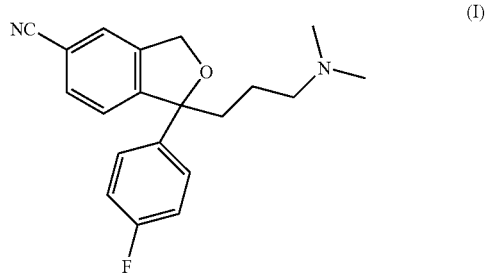
(I)

which comprises the cyclisation reaction of the compound of the formula

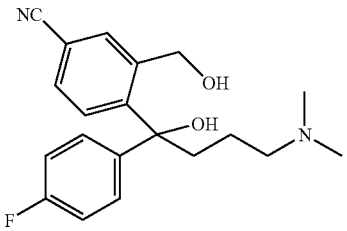

(III)

characterised in that said cyclisation reaction is performed in the presence of an azodicarboxylate, a phosphine and a strong base.

A preferred embodiment of the present invention provides a process for the preparation of escitalopram of the formula

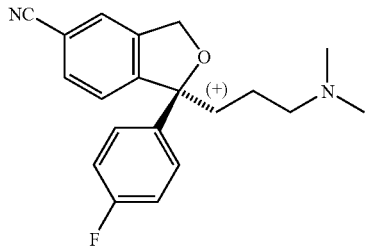

(II)

which comprises the cyclisation reaction of the compound of the formula

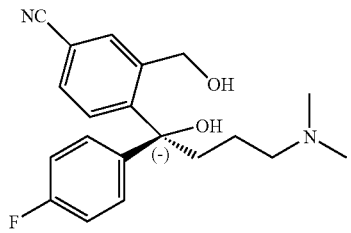

(IV)

characterised in that said cyclisation reaction is performed in the presence of an azodicarboxylate, a phosphine and a strong base.

DETAILED DESCRIPTION OF THE INVENTION

The process provided by the present invention provides the cyclisation reaction of the compounds of the above-stated formula III or, preferably, IV.

The compound of the formula III may be prepared, for example, as described in Example 1 of U.S. Pat. No. 4,650,884.

The compound of the formula IV may be prepared, for example, according to one of the two methods described in EP347066, which methods are substantially based on the separation of diastereomers.

More particularly, the first method provides esterification of the compound of the formula III (racemic diol) with an enantiomerically active acyl chloride, with formation of 2 diastereomeric esters which may be separated by means of HPLC (method (a), Example 1 of EP347066).

The second procedure, on the other hand, provides fractional crystallisation of said compound of the formula III (racemic diol) by using optically active tartaric acid (Example 2 of EP347066).

The compound of the formula IV may preferably be prepared as described, in contrast, in Italian patent application MI2004A000717 by enzymatic resolution, using an esterase obtained from *Aspergillus niger*, of the racemic mixture of compound of the formula

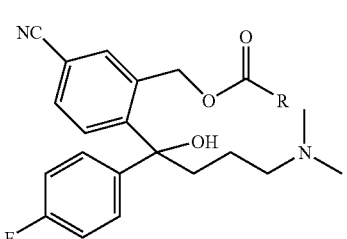

(V)

in which R represents $C_1$-$C_{12}$, preferably $C_1$-$C_4$, more preferably $C_1$ alkyl, or aryl to yield the compound of the formula

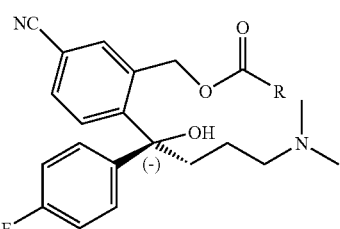

(VI)

The (−)enantiomer of the formula VI obtained in this manner may be then converted by means of hydrolysis, preferably basic hydrolysis, into the optically active diol of the formula IV.

Similarly, the compound of the formula IV may be prepared as described in WO04/014821, which is incorporated herein by reference, by selective enzymatic hydrolysis of analogues of the compounds of the formula VI, in particular of acylthio derivatives or carbamoyl derivatives, preferably carbamoyl derivatives. See formula IV on page 81 of said international patent application for a clear definition of these compounds and the meanings assumed by W and $l^3$, which, for the acylthio derivatives, are W=S and $R^3$=$YR^1$, with Y being a bond, while for the carbamoyl derivatives W=O, $R^3$=$YR^1$, with Y=NH. In both cases, $R^1$ assumes the meanings stated on page 78, line 14 to page 79, line 2 of the above-stated international patent application.

The process according to the present invention provides the cyclisation reaction of the compound of the formula III or, preferably, IV in the presence of an azodicarboxylate, a phosphine and a strong base.

In general, in the present process, the azodicarboxylate is preferably diethyl azodicarboxylate (DEAD) or is selected from among diisopropyl azodicarboxylate (DIAD), di-tert.-butyl azodicarboxylate, 1,1-azodicarbonyldipiperidine and is generally used in a molar ratio of between 7:1 and 4:1, preferably in molar ratio of around 5.3:1, per mole of substrate of the formula III or, preferably, IV.

The triarylphosphines used in the present cyclisation reaction are unsubstituted, such as for example triphenylphosphine, or substituted, such as for example p-trichlorotriphenylphosphine or p-trimethoxytriphenylphosphine, preferably triphenylphosphine, in a molar ratio of between 5:1 and 2:1, preferably in a molar ratio of around 3:1, per mole of substrate of the formula III or, preferably, IV.

In general, the reaction is performed in the presence of a strong base, preferably selected from among alkali metal alkoxylates, such as for example sodium and potassium tert.-butylate, sodium methylate or sodium ethylate, preferably sodium tert.-butylate, in a molar ratio of between 3:1 and 1:1, preferably of around 2.4:1 per mole of substrate of the formula III or, preferably, IV.

The above-mentioned cyclisation reaction is preferably carried out in a solvent selected from among aromatic solvents, such as toluene or benzene, ethers, such as tetrahydrofuran (THF), or chlorinated solvents, such as dichloromethane, preferably in tetrahydrofuran, in a volume of between 10 and 20 litres, preferably of around 15 litres per mole of substrate of the formula III or, preferably, IV. The cyclisation reaction is generally performed at a temperature of between −10° C. and +30° C., preferably of around 0° C.

The reaction is usually terminated by treatment with water and subsequently, after extraction with an organic solvent, preferably toluene, at a basic pH, indicatively of around a value of 9.0, citalopram (I) or escitalopram (II) is obtained as a free base or, preferably, they are isolated in salified form by treatment with the appropriate acid, for example in the form of citalopram hydrobromide or escitalopram oxalate.

The present process is particularly advantageous when used to prepare escitalopram (II), since it permits cyclisation of the diol IV with elevated stereoselectivity, minimising the formation of the inactive R(−) enantiomer. In a particularly preferred embodiment, the compound of the formula IV is dissolved in tetrahydrofuran and, at a temperature of around 0° C., triphenylphosphine dissolved in tetrahydrofuran is added, ethyl azodicarboxylate and sodium tert.-butylate dissolved in tetrahydrofuran are separately added dropwise to the mixture, which is stirred overnight. 1 N hydrochloric acid is then added dropwise and the mixture is evaporated. After addition of toluene and water to the residue, the pH is adjusted to a value of between 8.5 and 10, preferably to a value of around 9.4, by addition of aqueous ammonia. The phases are separated and the organic phase is evaporated under a vacuum. If oxalic acid is added to the residue, a solid is obtained which corresponds to the enantiomer (+)-1-(3-dimethylaminopropyl)-1-(4'-fluorophenyl)-1,3-dihydro-5-isobenzofurancarbonitrile oxalate(escitalopram).

For the purposes of the present invention, the terms "racemic mixture", "racemate", "racemic compound" are taken to mean not only 50:50 mixture of the two individual enantiomers, but also a mixture in which one of the two enantiomers is present in excess relative to the other enantiomer.

The following Examples are provided purely by way of illustration and should not be considered to limit the invention.

EXAMPLES

Example 1

Synthesis of (+)-1-(3-dimethylaminopropyl)-1-(4'-fluorophenyl)-1,3-dihydro-5-isobenzofurancarbonitrile oxalate (II, escitalopram)

2.8 g (0.081 moles) of (−)-4-(4-dimethylamino)-1-(4'-fluorophenyl)-1-(hydroxybutyl)-3-(hydroxymethyl)benzonitrile and 6.43 g of triphenylphosphine (0.0245 moles, equivalent to 3 moles per mole of starting substrate) dissolved in 100 ml of tetrahydrofuran are introduced into a 4-necked flask under a nitrogen atmosphere at 0° C., and stirring is started. 6.8 ml of ethyl azodicarboxylate (0.043 moles, equivalent to 5.3 moles per mole of starting substrate) dissolved in 20 ml of tetrahydrofuran and 1.86 g sodium tert.-butylate (0.01944 moles) dissolved in 15 ml of tetrahydrofuran are slowly added dropwise. The mixture is left overnight with stirring and the reaction is then terminated by dropwise addition of 30 ml of 1N HCl. The mixture is evaporated, 70 ml of toluene and 70 ml of water are added and the pH is adjusted to 9.4 by addition of aqueous ammonia. The phases are separated and the organic phase is evaporated under a vacuum. An oil (2.2 g) is obtained, to which 5 ml of acetone are added, 0.94 g of oxalic acid are added, and the mixture is filtered, giving rise to 2 g of escitalopram oxalate with $[\alpha]_D$=+15.4 (molar yield 59.5%).

Example 2

Synthesis of 1-(3-dimethylaminopropyl)-1-(4'-fluorophenyl)-1,3-dihydro-5-isobenzofurancarbonitrile hydrobromide (I, citalopram)

7.2 g of 4-(4-dimethylamino)-1-(4'-fluorophenyl)-1-(hydroxybutyl)-3-(hydroxymethyl)benzonitrile (0.021 moles) are dissolved in 200 ml of tetrahydrofuran; 16.54 g of triphenylphosphine (0.0630 moles) are added to the solution with stirring. 12.9 ml of ethyl azodicarboxylate (0.081 moles, equivalent to 3.8 moles per mole of starting substrate) dissolved in 50 ml of tetrahydrofuran are added dropwise at 0° C., 4.83 g of sodium tert.-butylate (0.05 moles, equivalent to 2.5 moles per mole of starting substrate) are added dropwise and the mixture is left overnight. The reaction is terminated by addition of 70 ml of a solution of 1N HCl, the mixture is evaporated to leave a residue, 150 ml of water and 150 ml of toluene are added and the phases are separated. 150 ml of toluene are added to the aqueous phase and the pH is adjusted to 9.4 by addition of 30% strength aqueous ammonia. The phases are separated, the organic phase is evaporated, the residue is dissolved in 15 ml of acetone and 62% strength HBr is added until a pH value of 1 is obtained. The mixture is filtered, giving rise to 5 g of crude 1-(3-dimethylaminopropyl)-1-(4'-fluorophenyl)-1,3-dihydro-5-isobenzofurancarbonitrile hydrobromide (I, citalopram).

The solid is dissolved in 10 ml of demineralised water, heated and left overnight at ambient temperature. 3.5 g of 1-(3-dimethylaminopropyl)-1-(4'-fluorophenyl)-1,3-dihydro-5-isobenzofurancarbonitrile hydrobromide (I, citalopram) are obtained with purity of 99.85%, determined by HPLC analysis, (molar yield=42%).

$^1$H-NMR (DMSO-d6) 1.48-1.39 (m, 1H), 1.57-1.49 (m, 1H), 2.25-2.21 (t, 1H), 2.69 (s, 6H), 3.05-3.01 (t, 2H), 5.18-5.15 (d, 1H), 5.26-5.22 (d, 1H), 7.21-7.16 (m, 2H), 7.61-7.57 (m, 2H), 7.77-7.75 (d, 1H), 7.83-7.81 (s, 1H), 9.14 (s, 1H).

The invention claimed is:

1. A process for the preparation of escitalopram of formula

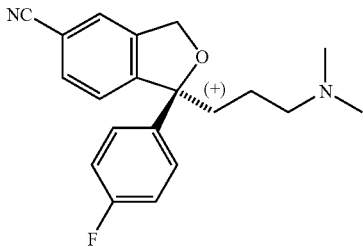

(II)

comprising cyclizing the compound of formula

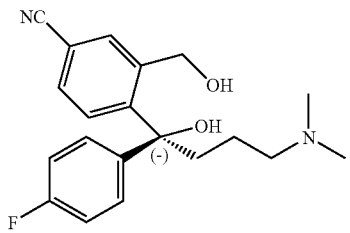

(IV)

in the presence of an azodicarboxylate, a phosphine and a strong base.

2. The process of claim 1 which further comprises prior to said cyclizing, enzymatically resolving a racemic mixture of a compound of formula

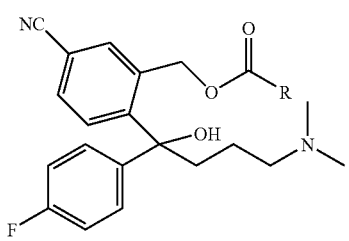

(V)

where R represents $C_1$-$C_{12}$ alkyl, or aryl, using an esterase obtained from *Aspergillus Niger*, to yield a compound of formula

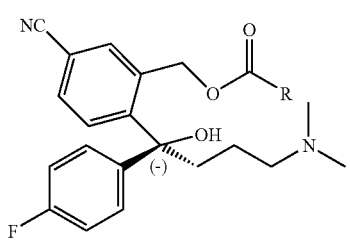

(VI)

and, hydrolyzing the compound of formula (VI) to yield the compound of the formula IV.

3. The process of claim 2, wherein R represents $C_1$-$C_4$ alkyl.

4. The process of claim 1, wherein said azodicarboxylate is selected from the group consisting of diethyl azodicarboxylate (DEAD), diisopropyl azodicarboxylate (DIAD), di-tert.-butyl azodicarboxylate and 1,1-azodicarbonyldipiperidine.

5. The process of claim 4, wherein said azodicarboxylate is diethyl azodicarboxylate.

6. The process of claim 1, wherein the amount of said azodicarboxylate is in a molar ratio of between about 7:1 and 4:1 per mole of substrate of formula IV.

7. The process of claim 6, wherein the amount of said azodicarboxylate is in a molar ratio of about 5.3:1 per mole of substrate of formula IV.

8. The process of claim 1, wherein said phosphine is a triarylphosphine selected from the group consisting of triphenylphosphine, p-trichlorotriphenylphosphine and p-trimethoxytriphenylphosphine.

9. The process of claim 8, wherein said triarylphosphine is triphenylphosphine.

10. The process of claim 1 wherein the amount of said phosphine is in a molar ratio of between about 5:1 and 2:1 per mole of substrate of formula IV.

11. The process of claim 10, wherein the amount of said phosphine is in a molar ratio of about 3:1 per mole of substrate of formula IV.

12. The process of claim 1 wherein said strong base is selected from the group consisting of sodium tert-butylate, potassium tert-butylate, sodium methylate and sodium ethylate.

13. The process of claim 12, wherein the strong base is sodium tert-butylate.

14. The process of claim 1, wherein the amount of said strong base is in a molar ratio of between about 3:1 and 1:1 per mole of substrate of formula IV.

15. The process of claim 14, wherein the amount of said strong base is in a molar ratio of about 2.4:1 per mole of substrate of formula IV.

16. The process of claim 1 wherein said cyclizing is carried out in a solvent selected from the group consisting of aromatic solvents, ethers and chlorinated solvents.

17. The process of claim 16, wherein said solvent is tetrahydrofuran.

18. The process of claim 16, wherein the amount of said solvent is between about 10 and 20 litres per mole of substrate of formula IV.

19. The process of claim 1 wherein said cyclizing is carried out at a temperature of between about −10° C. and +30° C.

20. The process of claim 19 wherein said cyclizing is carried out at a temperature of about 0° C.

21. The process of claim 18, wherein the amount of said solvent is about 15 litres per mole of substrate of formula IV.

* * * * *